US00PP10666P

United States Patent [19]

Meilland

[11] Patent Number: Plant 10,666

[45] Date of Patent: Nov. 3, 1998

[54] MINIATURE ROSE PLANT NAMED 'MEIDONFE'

[75] Inventor: Alain A. Meilland, Antibes, France

[73] Assignee: The Conard-Pyle Company, West Grove, Pa.

[21] Appl. No.: 796,904

[22] Filed: Feb. 6, 1997

[51] Int. Cl.[6] ..... A01H 5/00

[52] U.S. Cl. ..... Plt./10

[58] Field of Search ..... Plt./7.1, 10

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly forms attractive double red flowers. A bushy growth habit is exhibited. The plant propagates well from cuttings. The blossoms possess no fragrance. The plant can be grown as attractive ornamentation in the landscape or as a decorative pot plant.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the product of the pollination of the 'Meijikatar' variety U. S. Plant Pat. No. 4,682) and the 'Meirutral' variety (U. S. Plant Pat. No. 7,021). The male parent (i.e., the pollen parent) of the new variety was the 'Ruimired' variety (U. S. Plant Pat. No. 5,770). The parentage of the new variety can be summarized as follows:

('Meijkatar'×'Meirutral')×'Ruimired'.

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms in abundance attractive double red flowers,
(b) exhibits a bushy growth habit,
(c) propagates well on its own roots, and
(d) is particularly suited for growing as an ornamental pot plant.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meidonfe' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during April while growing on their own roots indoors at LeCannet des Maures, Var, France.

FIG. 1—illustrates a specimen of a young shoot;

FIG. 2—illustrates specimens of floral buds before the opening of the sepals;

FIG. 3—illustrates specimens of two floral buds at the opening of the sepals;

FIG. 4—illustrates specimens of two floral buds at the opening of the petals;

FIG. 5—illustrates specimens of two flowers during the course of opening;

FIG. 6—illustrates a specimen of an open flower —plan view — obverse;

FIG. 7—illustrates a specimen of an open flower —plan view — reverse;

FIG. 8—illustrates a specimen of a fully open flower —plan view obverse;

FIG. 9—illustrates a specimen of a fully open flower —plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets with the upper surface being shown at the right and the under surface being shown at the left;

FIG. 15—illustrates specimens of leaves with five leaflets with the upper surface being shown at the top and the under surface being shown at the bottom; and FIG. 16—illustrates specimens of leaves with seven leaflets with the upper surface being shown at the upper-left and the under surface being shown at the lower-right.

DETAILED DESCRIPTION

Figures 1, 2, 3, 4, 5, 6, 7, 8, 9, 10, 11, 12, 13, 14, 15, 16:
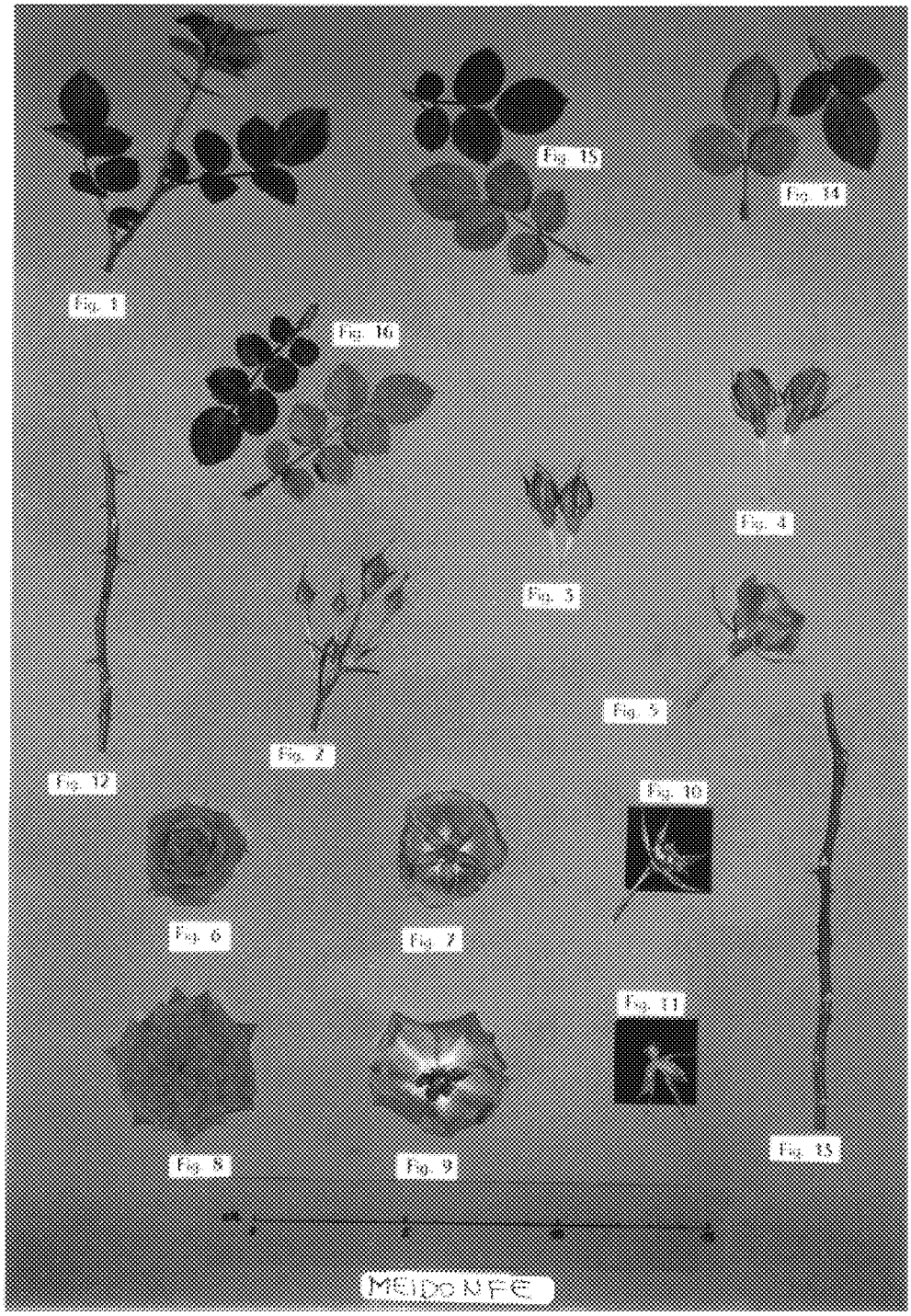

The chart used in the identification of the colors is that of The Royal Horticultural Society (R.H.S. Colour Chart). The terminology which precedes reference to the chart has been added to indicate the corresponding colors in more common terms. The description is based on one year-old specimens of the new variety which were observed during April while growing on their own roots indoors at LeCannet des Maures, Var, France.

Class: Miniature.

Plant:

*Height*.—approximately 30 cm. on average at the end of the growing season.

*Habit*.—Bushy.

Branches:

*Color*.—Young stems: Lettuce Green, Yellow-Green Group 144A. Adult wood: Green Group 137A.

*Thorns*.—Size: small. Quantity: numerous. Color: greenish to pinkish.

Leaves:

*Petioles*.—Upper surface: striped, reddish on young foliage and medium green on mature foliage with more or less glandular edges. Under surface: light green and bear some small thorns.

*Stipules*.—Adnate, pectinate, rather narrow and linear.

*Leaflets*.—Number: 3, 5, and 7 (most often). Shape: rounded. Texture: consistent. General appearance: dense, medium green, and glossy foliage. Color (young foliage): upper surface: Lettuce Green, Yellow-Green Group 144A with reddish edges. under surface: Lettuce Green, Yellow-Green Group 144A with reddish edges. Color (adult foliage): upper surface: dark green, Green Group 137A. under surface: medium green, Yellow-Green Group 147B.

Inflorescence:

*Number of flowers*.—Commonly approximately 2 to 5 per stem in clusters.

*Peduncle*.—Medium green in coloration, and the length is approximately 3 cm. on average.

*Sepals*.—Upper surface: tomentose, possess an elongated lanceolate configuration, average in size with some relatively small extensions (as illustrated) and greenish in coloration. Under surface: light green in coloration and commonly without extensions.

*Buds*.—Shape: egg-shaped. Length: approximately 1.5 on average. Size: medium. Color upon opening: upper surface: Cardinal Red, near Red Group 53A. under surface: Currant Red, near Red Group 46A.

*Flower*.—Form: flattened convex. Diameter: approximately 5.5 cm. on average. Color (when opening begins): upper surface: near Red Group 53D. under surface: near Yellow Group 10A and widely suffused with Red Group 53A with a light pink line extending along the middle. Color (when blooming): upper surface: near Red Group 53D. under surface: near Yellow Group 10A and widely suffused with Red Group 53C with a light pink line extending along the middle. Color (at end of opening): upper surface: near Red-Purple Group 57B. under surface: near Red-Purple Group 57B. Fragrance: none. Petal number: approximately 50 on average. petal shape: rounded tip with an obtuse base and reflexed edges. Petal drop: good. Anthers: normal and ochre in coloration. Stamen number: approximately 40 on average. Filaments: normal and greenish in coloration. Pistil number: approximately 20 on average. Stigmas: yellowish in coloration. Styles: greenish in coloration. Receptacle: medium green, smooth, and in longitudinal section in the shape of a pear. Lasting quality: long, when grown indoors the blossoms commonly last approximately 12 to 15 days on the plant.

Development:

*Vegetation*.—Strong.

*Blooming*.—Very abundant and substantially continuous.

*Resistance to diseases*.—good.

*Resistance to frost*.—good.

I Claim:

1. A new and distinct variety miniature rose plant characterized by the following combination of characteristics:

(a) forms in abundance attractive double red flowers,
(b) exhibits a bushy growth habit,
(c) propagates well on its own roots, and
(d) is particularly suited for growing as an ornamental pot plant; substantially as herein shown and described.

* * * * *

MEIDO NPE